United States Patent [19]
Mollenauer et al.

[11] Patent Number: 5,514,109
[45] Date of Patent: May 7, 1996

[54] ADJUSTABLE VALVE HAVING A RADIALLY COMPRESSIBLE SEALING BODY

[75] Inventors: Kenneth H. Mollenauer, Santa Clara; George D. Hermann, Los Gatos; Thomas A. Howell, Palo Alto; Michelle Y. Monfort, Los Gatos, all of Calif.

[73] Assignee: Thomas J. Fogarty, Portola Valley, Calif.

[21] Appl. No.: 290,401

[22] Filed: Aug. 15, 1994

Related U.S. Application Data

[62] Division of Ser. No. 992,145, Dec. 17, 1992, Pat. No. 5,338,313.

[51] Int. Cl.⁶ .................................................. A61M 5/00
[52] U.S. Cl. ..................... 604/249; 604/256; 604/283; 251/4
[58] Field of Search ................................ 604/30, 33, 34, 604/243, 246, 249, 250, 256, 283; 251/4

[56] References Cited

U.S. PATENT DOCUMENTS

| | | | |
|---|---|---|---|
| 3,685,786 | 8/1972 | Woodson | 251/4 |
| 3,977,400 | 8/1976 | Moorehead | |
| 4,723,550 | 2/1988 | Bales et al. | 128/344 |
| 5,098,396 | 3/1992 | Taylor et al. | 604/169 |
| 5,279,597 | 1/1994 | Dassa et al. | 604/283 |

FOREIGN PATENT DOCUMENTS

| | | |
|---|---|---|
| 3324699 | 12/1984 | Germany . |
| WO84/01902 | 5/1984 | WIPO . |

*Primary Examiner*—Corrine McDermott
*Attorney, Agent, or Firm*—Townsend and Townsend and Crew

[57] ABSTRACT

An adjustable surgical valve has a sealing body with an axial passage extending through it, a toroidal body axially aligned with the sealing body, and a device that selectively changes the relative axial positions of the sealing body and the toroidal body. The sealing body and the toroidal body have mating surfaces which radially compresses the axial passage of the sealing body when the relative axial positions of the sealing body and the toroidal body are changed. This causes the axial passage to seal with an instrument inserted into it, or the seal with itself if no instrument is inserted. Alternatively, or additionally, the sealing body may include a braided sleeve coaxial with the axial passage and extending from the sealing body, and a device that selectively changes the relative axial positions of the sealing body and the extended part of the braided sleeve to elongate the braided sleeve. This causes the braided sleeve to contract radially, which compresses the axial passage of the sealing body radially. The sealing body is made of an elastomeric foam or an encapsulated gel.

19 Claims, 4 Drawing Sheets

ADJUSTABLE VALVE HAVING A RADIALLY COMPRESSIBLE SEALING BODY

This is a Division of application Ser. No. 07/992,145 filed Dec. 17, 1992 now U.S. Pat. No. 5,338,313.

BACKGROUND OF THE INVENTION

In cardiac, vascular, urology, laparoscopic cholecystectomy and other medical procedures using catheters, there has been an increasing need for large-diameter valves. These procedures use catheters having a wide range of diameters. These procedures may also use multiple catheters.

Current surgical valves fall into two basic categories, passive and active. A passive valve relies on the deformation of a resilient part by the catheter to form the required fluid-tight seal with the catheter. A recent example of a passive valve is described in U.S. Pat. No. 4,909,798, in which the valve has a longitudinally extended valve housing with a first opening and a central longitudinal passage communicating with an opposite second opening. A one-piece seal located in the longitudinally extended valve housing has a sealing neck having a relatively small opening that communicates with a sealing chamber. On the opposite side of the sealing chamber are sealing exit lips that are readily expansible to a diameter less than that of the valve housing when a catheter is inserted. This surgical valve does not accommodate a wide range of catheter diameters. A seal that exerts enough lateral pressure to seal around a small-diameter catheter applies too much friction when sealing a large-diameter catheter. Moreover, the lip-type seals tend not to seal uniformly around all of the circumference of the catheter.

An active surgical valve includes a mechanism that moves a seal into contact with the catheter when the catheter is in place in the valve. A common feature of such valves is a tube of a flexible material through which the catheter is inserted. A mechanism moves the flexible material into contact with the catheter.

Some valves, such as the valves shown in U.S. Pat. Nos. 3,977,400 and 4,243,034, use a simple vise-like arrangement with opposing jaws to bring the flexible material into contact with the catheter. With such an arrangement, the contact pressure between the flexible material and the catheter is very non-uniform around the circumference of the catheter. A development of this arrangement uses two pairs of opposing jaws perpendicular to one another to produce a more uniform contact pressure.

U.S. Pat. No. 3,970,089 describes a tube of a flexible material surrounded by an annular vessel into which a fluid can be pumped to apply pressure to the outer wall of the tube, and hence to move the inner wall of the tube into contact with the catheter. This arrangement provides a uniform contact pressure between the tube and the catheter, but the range of catheters that can be sealed without the wall of the tube buckling, and providing a leakage path, is limited.

U.S. Pat. No. 4,580,573 shows an arrangement in which a flexible tube has a rigid tube connected to each end. The catheter passes through the rigid tubes and the flexible tube. By rotating one of the rigid tubes axially relative to the other a twist is imposed on the flexible tube, which reduces the internal diameter of the flexible tube such that the inner wall of the flexible tube forms a seal with the catheter.

Current surgical valves have a tendency to leak, especially if multiple catheters are used. Additionally, current surgical valves can only be used with catheters having a relatively narrow range of diameters. Current large diameter surgical valves do not close completely and require that the catheter be left in place to maintain a seal. Current surgical valves require constant manipulation to maintain a seal around the catheter without excessive friction.

OBJECTS AND SUMMARY OF THE INVENTION

An adjustable surgical valve according to a first aspect of the invention comprises a sealing body that has an axial passage extending through it, a toroidal body that is axially aligned with the sealing body, and a device that selectively changes the relative axial positions of the sealing body and the toroidal body. The sealing body and the toroidal body have mating surfaces which radially compress the axial passage of the sealing body when the relative axial positions of the sealing body and the toroidal body are changed. Radially compressing the axial passage causes the axial passage to seal with an instrument inserted into it; or to seal with itself if no instrument is inserted into the axial passage.

An adjustable surgical valve according to a second aspect of the invention comprises a sealing body that has an axial passage extending through it. The sealing body includes a braided sleeve that is coaxial with the axial passage and that extends from the sealing body. The valve also comprises a device that selectively changes the relative axial positions of the sealing body and part of the braided sleeve remote from the sealing body. Changing the relative axial positions of the sealing body and the remote part of the braided sleeve elongates the braided sleeve, which causes the braided sleeve to contract radially, and compresses the axial passage of the sealing body radially. Radially compressing the axial passage causes the axial passage to seal with an instrument inserted into it; or to seal with itself if no instrument is inserted into the axial passage.

In a first practical embodiment of an adjustable surgical valve according to the invention, the mating surface of the sealing body is its outer surface and the mating surface of the toroidal body is its inner surface. In the plane perpendicular to the axis defined by the axial passage in the sealing body ("the axis"), the distance of the outer surface of the sealing body from the axis is substantially constant. In the same plane, the distance of inner surface of the toroidal body from the axis decreases along the axis from greater than the distance of the outer surface of the sealing body from the axis to less than the distance of the outer surface of the sealing body from the axis. The sealing body is located in a substantially fixed axial position by a braided sleeve, and the means for selectively changing the relative axial positions of the sealing body and the toroidal body moves the toroidal body axially relative to the sealing body.

When the valve is in its open (non-sealing) position, the mating surfaces of the sealing body and the toroidal body are substantially disengaged. The valve is closed by moving the toroidal body axially into engagement with the sealing body such that, as the toroidal body is moved, the distance from the axis of the inner surface of the toroidal body engaged with a given point on the sealing body progressively decreases. The rigid inner surface of the toroidal body thus deforms the compliant outer surface of the sealing body radially towards the axis. The toroidal body additionally elongates the braided sleeve. The resulting compression of the sealing body compresses the axial passage and forms the required seal.

The valve is opened by moving the toroidal body axially relative to the sealing body in the opposite direction, i.e., such that the distance from the axis of the inner surface of the toroidal body engaged with a given point on the sealing body progressively increases. This reduces the radial deformation of the outer surface of the sealing body and the elongation of the braided sleeve, which reduces the deformation of the axial passage, and releases the seal. The means for changing the relative positions of the sealing body and the toroidal body in the first practical embodiment of the valve includes a ratchet mechanism.

In a second practical embodiment of an adjustable surgical valve according to the invention, the mating surface of the sealing body is its outer surface and the mating surface of the toroidal body is its inner surface. In the plane perpendicular to the axis, the distance of the inner surface of the toroidal body from the axis is substantially constant. In the same plane, the distance of the outer surface of the sealing body increases along the axis, from less than the distance of the inner surface of the toroidal body from the axis to greater than the distance of the inner surface of the toroidal body from the axis. The sealing body includes a braided sleeve. The toroidal body has a fixed position and the means for selectively changing the relative axial positions of the sealing body and the toroidal body moves the sealing body axially relative to the sealing body.

When the valve is in its open (non-sealing) position, the mating surfaces of the sealing body and of the toroidal body are substantially disengaged. The valve is closed by moving the sealing body axially to bring its outer surface into engagement with the inner surface of the toroidal body such that, as the sealing body is moved, the distance from the axis of the outer surface of the sealing body engaged with a given point on the inner surface of the toroidal body progressively increases. Because the inner surface of the toroidal body is rigid, it deforms the outer surface of the sealing body radially towards the axis. The axial motion of the sealing body also elongates the braided sleeve. The resulting compression of the sealing body compresses the axial passage and forms the required seal.

The valve is opened by moving the sealing body axially relative to the toroidal body in the opposite direction, i.e., such that the distance from the axis of the outer surface of the sealing body engaged with a given point on the inner surface of the toroidal body progressively decreases. This reduces the radial compression applied to the sealing body and releases the seal. The means for changing the relative positions of the sealing body and the toroidal body in the second practical embodiment of the hemostasis valve according to the invention includes a mechanism that translates a twisting motion to an axial motion.

Practical embodiments of an adjustable surgical valve according to the invention employ both mating surfaces and axial stressing of a braided sleeve to apply a uniform radial compression to the axial passage in the sealing body.

It is an object of the invention to provide an adjustable surgical valve that can be adjusted to seal around instruments having a wide range of diameters without leaking.

It is a further object of the invention to provide an adjustable surgical valve that provides a seal that is both liquid-tight and gas-tight.

It is a further object of the invention to provide an adjustable surgical valve that provides good tactile feedback without leaking.

It is a further object of the invention to provide an adjustable surgical valve that seals around multiple instruments.

It is a further object of the invention to provide an adjustable surgical valve that can easily be adjusted using one hand.

It is a further object of the invention to provide an adjustable surgical valve that, once adjusted to seal around a given instrument, does not require further adjustment to maintain the seal.

It is a further object of the invention to provide an adjustable surgical valve that is self-sealing when the instrument is withdrawn.

In a first method of manufacturing an adjustable surgical valve according to the invention, a sealing body is attached inside the one end of a braided sleeve, the other end of the braided sleeve is threaded through the bore of a toroidal body, and the braided sleeve, toroidal body, and sealing body are inserted into the bore of a substantially cylindrical valve body. In a variation on the first method, the sealing body is attached to the braided sleeve by molding it in place in the braided sleeve.

In a second method of manufacturing an adjustable surgical valve according to the invention, a braided sleeve is inserted into the bore of a collar and the collar is attached to the braided sleeve part-way along the length of the braided sleeve. An elastomeric foam sealing body is molded along the length of, coaxial with, and surrounding the braided sleeve, and the sealing body is inserted into a cylindrical valve body.

DETAILED DESCRIPTION OF THE INVENTION

Figure 1A:
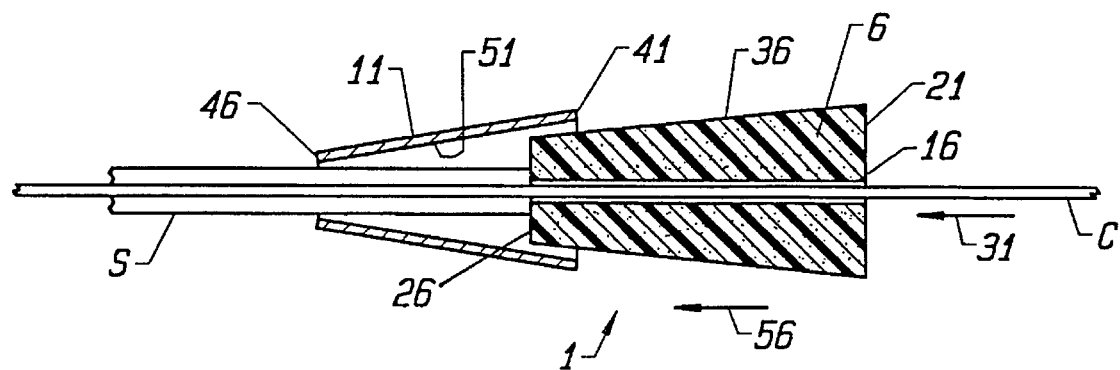
FIG. 1A is a longitudinal cross sectional view of the sealing mechanism of an adjustable surgical valve according to the first aspect of the invention in its open (non-sealing) position.
Figure 1B:
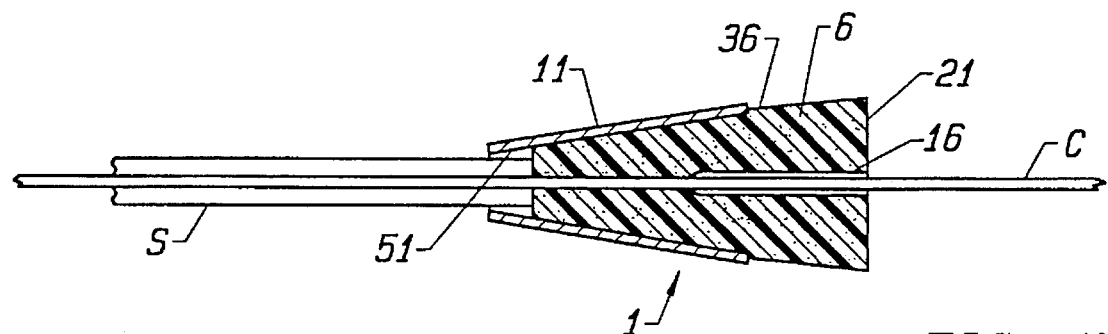
FIG. 1B is a longitudinal cross sectional view of the sealing mechanism of an adjustable surgical valve according to the first aspect of the invention in its closed (sealing) position.

The basic sealing mechanism of an adjustable surgical valve according to a first aspect of the invention is illustrated in FIGS. 1A and 1B. FIG. 1A shows the valve in its open (non-sealing) position. The adjustable surgical valve 1 has a sealing body 6, a toroidal body 11, and a mechanism (not shown) for changing the axial position of at least one of the sealing body 6 and the toroidal body 11 relative to the other.

The sealing body has an outer surface 36 that is its mating surface. The sealing body has an axial passage 16 through which one or more instruments, such as the catheter C, can be passed from the proximal end 21 of the sealing body to the distal end 26, in the direction indicated by the arrow 31. Sealed to the distal end 26 of the sealing body is the introducer sleeve S through which the catheter C passes into the body (not shown). The catheter C is shown throughout as an example of an instrument that is inserted into the axial passage of the valve. The valve can be used with instruments other than catheters, however.

The sealing body 6 is preferably formed of a resilient elastomeric foam material that is compliant, but is sufficiently strong in compression to enable a substantially uniform radial deformation of the outer surface 36 of the sealing body towards the axis to move the wall of the axial passage 16 radially towards the axis to contact, and to form a seal with, the catheter C, or, if no catheter is in the axial passage, to contact itself and to seal the axial passage. The sealing body 6 may alternatively be formed of an encapsulated medical silicone gel, such as Dow Corning Q7-2147. The preferred encapsulation material is RTV, such as G.E. 118.

Preferably, the outer surface 36 of the sealing body intersects a plane perpendicular to the axis defined by the axial passage 16 ("the axis") to form a circle, but can form other suitable shapes such as a square, a rectangle, a hexagon, an octagon, etc.

The toroidal body 11 is axially aligned with the sealing body 6, and has a proximal end 41 and a distal end 46. The toroidal body 11 is formed of a relatively rigid material, such as plastic or metal. The mating surface of the toroidal body 11 is its inner surface 51. The intersection of the inner surface 51 of the toroidal body with a plane perpendicular to the axis preferably forms the same shape as the outer surface 36 of the sealing body, i.e., a circle, but can form other suitable shapes such as a square, a rectangle, a hexagon, an octagon, etc.

In FIG. 1A, the distance from the axis of the outer (mating) surface 36 of the sealing body is shown as progressively decreasing from the proximal end 21 of the sealing body to the distal end 26, and the distance from the axis of the inner (mating) surface 51 of the toroidal body is also shown as progressively decreasing from the proximal end 41 of the toroidal body to the distal end 46. However, if the distance from the axis of the outer surface 36 of the sealing body progressively decreases between the proximal end 21 and the distal end 26, the distance from the axis of the inner surface 51 of the toroidal body may be substantially constant along the axis. Alternatively, if the distance from the axis of the inner surface 51 of the toroidal body progressively decreases between the proximal end 41 and the distal end 46, the distance from the axis of the outer surface 36 of the sealing body may be substantially constant along the axis. In any of the three cases just stated, the distance from the axis of the inner surface 51 at the proximal end 41 of the toroidal body should be less than the distance from the axis of the outer surface 36 at the proximal end 21 of the sealing body, and greater than the distance of the outer surface 51 at the distal end 26 of the sealing body.

The toroidal body 11 can be made considerably shorter in the axial direction than shown in FIG. 1A. A ring with a square, rectangular, circular, or other suitable cross section in the plane of the axis can be used for the toroidal body 11. Alternatively, the toroidal body 11 can comprise a plurality of substantially spherical or cylindrical beads on a substantially circular axis in the plane perpendicular to the axis. Such an arrangement reduces friction by providing the toroidal body 11 with an inner surface that rolls over the outer surface 36 of the sealing body instead of sliding.

FIG. 1A shows the adjustable surgical valve 1 according to the invention in its open (non-sealing) position. The sealing body 6 and the toroidal body 11 are axially positioned such that the inner surface 51 of the toroidal body is disengaged from the outer surface 36 of the sealing body. The toroidal body 11 thus exerts no radial compression on the sealing body 6, the axial passage 16 in the sealing body is fully open, which allows the catheter C to be freely inserted or withdrawn.

FIG. 1B shows the adjustable surgical valve according to the invention in its closed (sealing) position. The relative axial positions of the sealing body 6 and the toroidal body 11 have been changed in the direction shown by the arrow 56 to engage the inner surface 51 of the toroidal body with the outer surface 36 of the sealing body. This change in the relative axial positions is brought about by a suitable mechanism (not shown) that moves the sealing body relative to the toroidal body, or moves the toroidal body relative to the sealing body, or moves the sealing body and the toroidal body relative to one another. The rigid inner surface 51 of the toroidal body deforms radially towards the axis the part of the outer surface 36 of the sealing body with which it is engaged. This applies a uniform radial compression to the sealing body. The material of the sealing body transmits the uniform radial compression applied by the deformation of the outer surface of the sealing body to the part of the axial passage 16 substantially opposite the deformed outer surface. The uniform radial compression deforms the axial passage radially inwards. FIG. 1B shows the axial passage deformed sufficiently to bring the wall of the axial passage into contact with, and to seal, the catheter C.

With the relative positions of the sealing body 6 and the toroidal body 11 adjusted to bring the wall of the axial passage 16 into sealing contact with the catheter C, the catheter is sealed by a relatively large area of the compliant material of the sealing body. This provides a leak-proof seal using a relatively small radial force between the sealing body and the catheter. The resulting small frictional force between the sealing body and the catheter gives excellent "feel" when the catheter is inserted or adjusted. In this adjustment condition, the catheter can be adjusted or withdrawn without having to adjust the relative positions of the sealing body and the toroidal body. This adjustment condition will be called the "minimum friction-no leakage" condition.

Further change in the relative axial positions of the sealing body 6 and the toroidal body 11 in the direction shown by the arrow 56 increases the uniform radial compression on the sealing body. This causes further deformation of the axial passage 16. The axial passage is deformed over more of its length, and the radial force between the wall of the axial passage 16 and the instrument, such as the catheter C, is increased. This increases the friction between the sealing body and the catheter C, but further reduces the possibility of leakage. Further change in the relative axial positions of the sealing body and the toroidal body in the direction shown by the arrow 56 enables the valve to seal with a smaller diameter catheter, or to seal with no catheter.

Figure 2A:
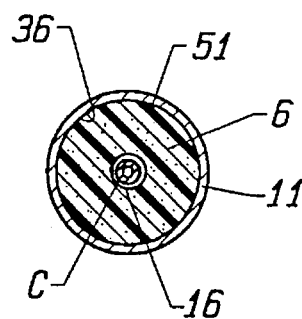
FIG. 2A is a transverse cross-sectional view of the sealing mechanism of an adjustable surgical valve according to the first aspect of the invention sealed around an instrument inserted into the axial passage of the valve.
Figure 2B:
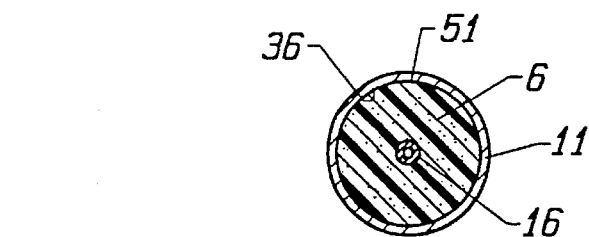
FIG. 2B is a transverse cross-sectional view of the sealing mechanism of an adjustable surgical valve according to the first aspect of the invention sealed after the instrument has been withdrawn.

Using an elastomeric foam or an encapsulated silicone gel to form the sealing body 6 enables the valve to accommodate a large diameter catheter and to seal without leaking when the large diameter catheter is withdrawn. The sealing body 6 also enables the valve to be self-sealing when the catheter is withdrawn. FIGS. 2A and 2B show cross sections of the valve in the plane perpendicular to the axis to illustrate the self-sealing action of the valve. In FIG. 2A, the relative axial positions of the toroidal body 11 and the sealing body 6 have been adjusted to deform the axial passage 16 such that its wall seals with the catheter C. FIG. 2B shows the valve after the catheter has been withdrawn. When the catheter is withdrawn, the resilience of the sealing body moves the wall of the axial passage further towards the axis, so that the wall seals with itself.

With a relatively small diameter catheter, the relative axial positions of the toroidal body 11 and the sealing body 6 can be adjusted to the minimum friction-no leakage position after the catheter is inserted, and the valve will be self-sealing without the need to readjust it when the catheter is withdrawn. In FIG. 2B, which shows the valve after the catheter has been withdrawn, the diameter of the outer surface 36 is the same as in FIG. 2A, which indicates that the relative positions of the toroidal body and the sealing body were not changed when the catheter was withdrawn.

With a larger diameter catheter, the relative positions of the toroidal body and the sealing body must be adjusted to produce a radial force on the axial passage 16 that is greater than the radial force for minimum friction for the valve to be self-sealing when the catheter is withdrawn.

Figure 3:
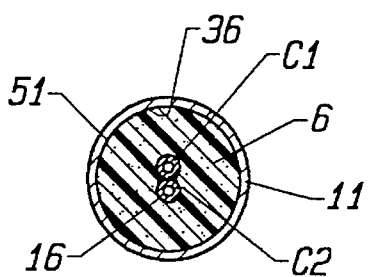
FIG. 3 is a transverse cross-sectional view of the sealing mechanism of an adjustable surgical valve according to the first aspect of the invention sealed around two instruments.

Using an elastomeric foam that is also compliant, or an encapsulated silicone gel, to form the sealing body 6 enables the surgical valve according to the invention to seal around two or more catheters inserted into the axial passage 16. This is illustrated in FIG. 3, which shows a cross-section of the valve in the plane perpendicular to the axis with two catheters C1 and C2 inserted into the axial passage 16. When the outer surface 36 of the sealing body 6 is radially deformed by the toroidal body 11, the resulting radial compression of the sealing body forces part of the sealing body to fill the narrow cusp between the two catheters and achieves the desired seal.

Figure 4A:
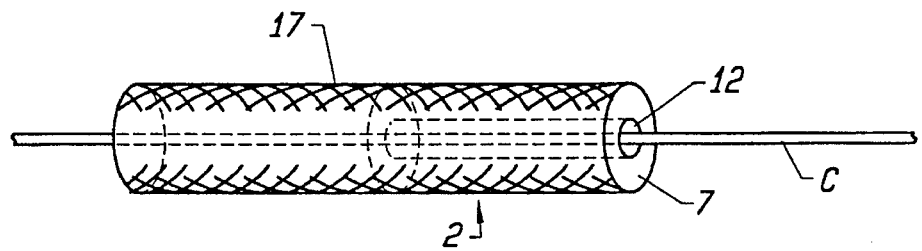
FIG. 4A is a perspective view of the sealing mechanism of an adjustable surgical valve according to the second aspect of the invention in its open (non-sealing) position.
Figure 4B:
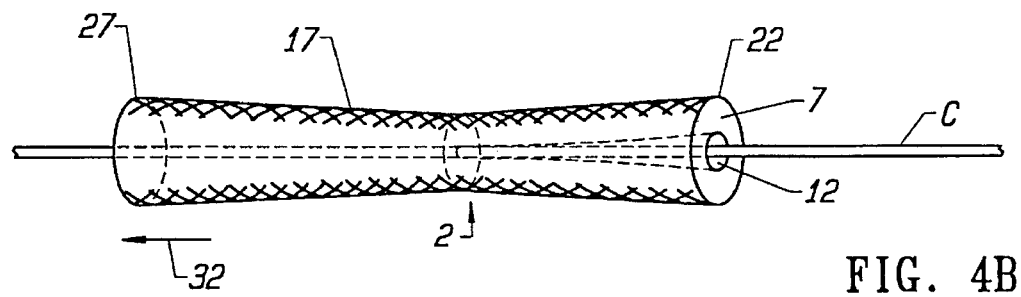
FIG. 4B is a perspective view of the sealing mechanism of an adjustable surgical valve according to the second aspect of the invention in its closed (sealing) position.
Figure 4C:
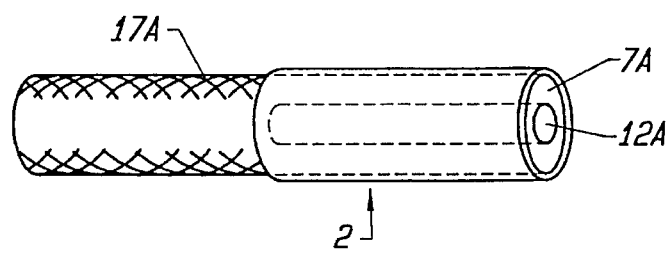
FIG. 4C is a perspective view of an alternative form of the sealing mechanism of an adjustable surgical valve according to the second aspect of the invention in its open (non-sealing) position.

FIGS. 4A through 4C show perspective views of the basic sealing mechanism of an adjustable surgical valve according to a second aspect of the invention. The adjustable surgical valve according to the second aspect of the invention is similar to the adjustable surgical valve according to the first aspect of the invention, but the uniform radial compression is applied to the sealing body in a different The adjustable surgical valve according to the second aspect of the invention is shown in its open (non-sealing) state in FIG. 4A. The adjustable surgical valve 2 comprises a substantially cylindrical sealing body 7. The sealing body includes a substantially cylindrical axial passage 12, through which one or more instruments, such as the catheter C, can be passed.

The sealing body 7 is formed from the same type of elastomeric foam material or encapsulated silicone gel as the sealing body 6 (FIG. 1) of the first embodiment of the invention. As with the sealing body of the first embodiment of the invention, the sealing body 7, when subject to a radial compression, forms a fluid-tight seal with one or more instruments passed through the axial passage 12. Details of the material of the sealing body 7 and of its sealing action are similar to those of the sealing body 6 (FIG. 1), and therefore will not be repeated.

The sealing body 7 preferably has a circular cross section in the plane normal to the axial passage. Unlike the sealing body of the first embodiment of the invention, the area of the circular cross section of the sealing body 7 is substantially constant along the length of the sealing body.

The sealing body 7 occupies part of the bore of the braided sleeve 17. The braided sleeve may be attached to the surface of the sealing body 7 with a suitable adhesive, or the sealing body may be molded inside the braided sleeve, with the braided sleeve providing the outer surface of the braided sleeve/sealing body assembly, as shown in FIG. 4A. Alternatively, the braided sleeve 17A may be incorporated within the sealing body 7A, as shown in FIG. 4C.

In FIG. 4A, the braided sleeve 17 is a hollow cylinder with a circular cross section that, when elongated, exerts a uniform radial compression. Anything placed inside the braided sleeve, such as the sealing body 7, is subject to the uniform radial compression when the braided sleeve is elongated. Thus, the braided sleeve subjects the sealing body to a uniform radial compression similar to that produced by the mating surfaces of the first embodiment of the invention.

The braided sleeve 17 is preferably made of a loosely-woven fabric, such as polyester, nylon, or polypropylene. To enable the braided sleeve to generate a uniform radial compression when elongated, the warp threads of the fabric are arranged at an angle relative to the longitudinal axis of the braided sleeve. Alternatively, the braided sleeve may be made of a knitted material.

In FIG. 4A, the sealing body 7 occupies part of the length of the braided sleeve 17. The braided sleeve is shown in its normal (non-elongated) state, and the sealing body 7 is not deformed. An instrument, such as the catheter C, placed in the axial passage 12 of the sealing body moves freely within the axial passage.

The effect of elongating the braided sleeve 17 on the sealing body 7 is illustrated in FIG. 4B, which shows the adjustable surgical valve 2 in its closed (sealing) state. Axially moving the part 27 of the braided sleeve distal from the sealing body relative to the sealing body in the direction shown by the arrow 32 elongates the braided sleeve and causes the braided sleeve to exert a uniform radial compression on the sealing body. The sealing body transmits the uniform radial compression exerted by the braided sleeve against its outer surface to the axial passage 12. The uniform radial compression deforms the axial passage, and causes it to seal with the catheter C. The magnitude of the radial compression is adjusted by changing the relative axial positions of the distal part 27 of the braided sleeve and the sealing body.

As an alternative to axially moving the distal part 27 of the braided sleeve relative to the fixed sealing body to elongate the braided sleeve 17, the distal part 27 of the braided sleeve can be fixed, and the sealing body 7 can be moved axially in the direction opposite to the direction indicated by the arrow 32. As a further alternative, both the sealing body and the distal part of the braided sleeve can be moved to elongate the braided sleeve.

Figure 5A:
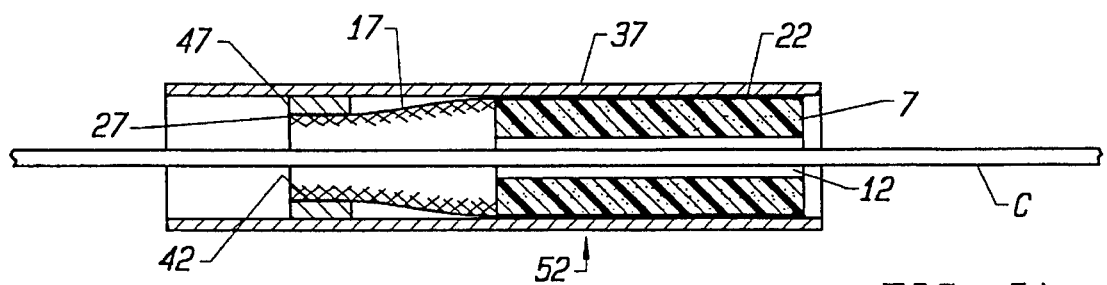
FIG. 5A is a longitudinal cross sectional view of a more complete embodiment of an adjustable surgical valve according to the second aspect of the invention in its open (non-sealing) position.
Figure 5B:
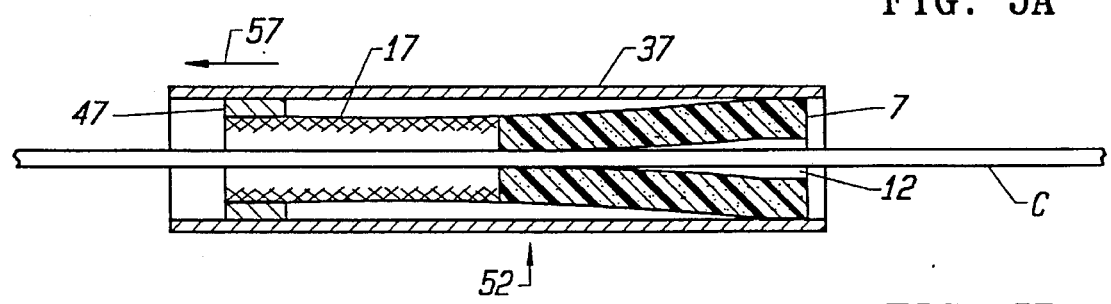
FIG. 5B is a longitudinal cross sectional view of a more complete embodiment of an adjustable surgical valve according to the second aspect of the invention in its closed (sealing) position.

Cross sections of a more complete embodiment of an adjustable surgical valve according to the second aspect of the invention are shown in FIGS. 5A and 5B. The sealing body 7 of valve 52 is formed inside the proximal part of the braided sleeve 17. The braided sleeve/sealing body assembly is mounted in the bore of the cylindrical valve body 37. The proximal part 22 of the braided sleeve/sealing body assembly is attached to the bore. The distal part 27 of the braided sleeve is attached to the inner surface 42 of the toroidal actuator 47.

The toroidal actuator 47 is free to slide axially within the bore of the valve body 37. A mechanism (not shown), attached to the toroidal actuator, adjusts the axial position of the toroidal actuator in the bore, and hence the elongation of the braided sleeve 17. Mechanisms of the type to be discussed below, or some other suitable mechanism, can be used to adjust the axial position of the toroidal actuator in the bore of the valve body.

FIG. 5A shows the adjustable surgical valve 52 in its open (non-sealing) state. The braided sleeve 17 is shown in its normal (non-elongated) state, and the sealing body 7 is not deformed. An instrument, such as the catheter C, placed in the axial passage 12 of the sealing body moves freely within the axial passage.

FIG. 5B shows the adjustable surgical valve 52 in its closed (sealing) state. The mechanism (not shown) has moved the toroidal actuator 47 in the bore of the valve body 37 in the direction of the arrow 57. This elongates the braided sleeve 17 and causes the braided sleeve to exert a uniform radial compression on the sealing body 7. The sealing body transmits the uniform radial compression exerted by the braided sleeve against its outer surface to the axial passage 12, which deforms the axial passage and causes it to seal with the catheter C. The magnitude of the radial compression is adjusted by changing the axial position of the toroidal actuator 47 in the bore of the valve body 37.

Practical embodiments of an adjustable surgical valve according to the invention employ both mating surfaces and elongation of a braided sleeve to apply a uniform radial compression to the axial passage in the sealing body.

Figure 6:
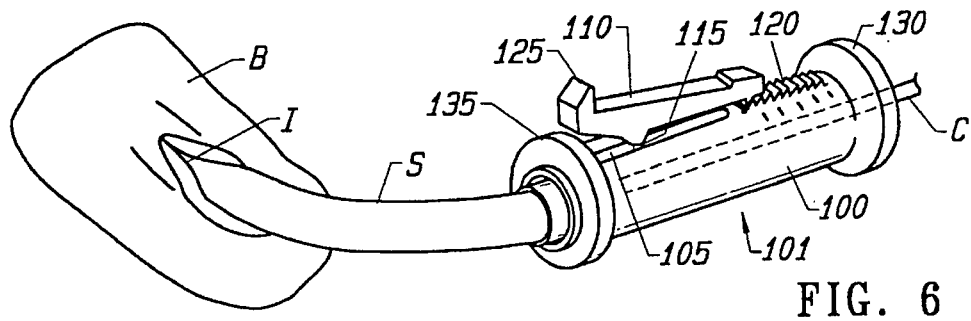
FIG. 6 is a perspective view of a first practical embodiment of an adjustable surgical valve according to the invention.

FIG. 6 shows a perspective view of the first practical embodiment of an adjustable surgical valve 101 according to the invention. The introducer sleeve S is attached to the distal end of the surgical valve 101, and passes through an incision or puncture I into the body B. A catheter C passes through the valve 101 and the introducer sleeve S into the body B.

The valve body 100 of the surgical valve is a hollow, substantially cylindrical plastic molding, preferably of polycarbonate. The bore of the valve body 100 has a circular cross section. A longitudinal slot 105 is molded or cut in the valve body 100. The pillar 115 passes through the slot 105 and is attached to the toroidal body (see FIG. 7). The end of the pillar distal from the toroidal body is inserted and glued into a small bore in the pawl 110. The pawl, which is preferably a polycarbonate molding, pivots by bending the pillar. The axis of the bore in the pawl is at an acute angle relative to the longitudinal axis of the pawl to bias the pawl into engagement with the ratchet 120. Alternatively, the pillar and pawl, or the pillar, pawl, and toroidal body can be molded as an integral unit.

Figure 7:
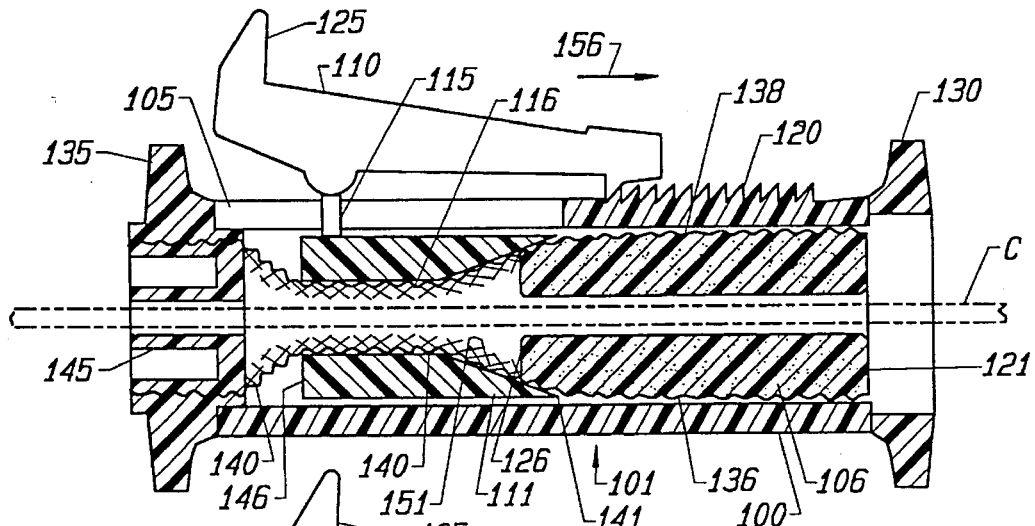
FIG. 7 is a longitudinal cross-sectional view of the first practical embodiment of an adjustable surgical valve according to the invention in its open (non-sealing) position.

The pawl 110, pillar 115, and ratchet 120 provide the preferred way of changing the relative axial positions of the sealing body 106 and the toroidal body 111 (FIG. 7) and of changing the elongation of the braided sleeve 138 (FIG. 7). This mechanism has a small number of parts, can be adjusted precisely, and can be operated with one hand. Alternative mechanisms can be used to change the relative axial positions of the sealing body and the toroidal body, and the elongation of the braided sleeve. For example, the twist mechanism to be described below in connection with FIGS. 10, 11, and 12 can be adapted to this purpose.

Pressure applied radially to the protrusion 125 on the pawl 110 disengages the pawl from the ratchet 120. The protrusion also facilitates axially sliding the pawl with the thumb to adjust the valve. The ratchet 120 is a metal stamping attached to the outer surface of the valve body 100 by gluing, preferably with an epoxy adhesive. Alternatively, the ratchet can be molded as an integral part of the valve body molding.

The flanged proximal and distal ends of the valve, 130 and 135, respectively, enable the valve to be gripped in the fingers of the hand while adjusting the position of the pawl with the thumb. The flanged ends are preferably integral parts of the valve body molding, but can be separate polycarbonate moldings glued to the valve body 100 with a cyanoacrylate or other suitable adhesive. The flanged end 135 must molded separately and later attached if the pawl, pillar and toroidal body are molded as an integral unit.

FIG. 7 shows a longitudinal cross-sectional view of surgical valve shown in FIG. 6. The sealing body 106 and the toroidal body 111 are mounted in the bore of the valve body 100. In the plane perpendicular to the axis defined by the axial passage 116 ("the axis"), the sealing body has a circular cross section. The diameter of the sealing body, i.e., the distance of the outer (mating) surface 136 of the sealing body from the axis, is substantially constant along the length of the sealing body. The diameter of the sealing body is reduced near its distal end 126 to enable the sealing body to engage smoothly with the toroidal body.

The toroidal body 111 is a polycarbonate molding with inner and outer circular cross sections in the plane perpendicular to the axis. Its outer diameter is slightly smaller than the diameter of the bore of the valve body 100, and is substantially constant along its length. This enables the toroidal body to slide freely within the bore of the valve body. The inner diameter of the toroidal body progressively decreases from the proximal end 141 of the toroidal body to about half-way along the toroidal body, and remains substantially constant from about half-way along the toroidal body to the distal end 146. If the pawl, pillar, and toroidal body are not molded as an integral unit, a small radial bore is provided in the toroidal body to receive the pillar 115, which is glued in place with a suitable adhesive.

The sealing body 106 is formed by molding or extruding a suitable silicone foam. The axial passage 116 is formed in the molding or extruding process. In the preferred embodiment, the sealing body is molded using Type 762 silicone foam from General Electric. The outer (mating) surface 136 of the sealing body is provided by the braided sleeve 138. The braided sleeve is a substantially cylindrical piece of woven polyester material that preferably is sealed with a silicone sealant, such as Type Q7-2213 sealant, manufactured by Dow Chemical Co.

The braided sleeve 138, after sealing, is placed in a mold and the silicone foam is injected into the mold inside the braided sleeve. When the completed sealing body/braided sleeve assembly is removed from the mold, the braided sleeve is firmly attached to the foam of the sealing body. Part of the braided sleeve forms the outer surface 136 of the sealing body. Alternatively, the foam can be molded separately and glued in place inside the braided sleeve using a silicone RTV or other suitable adhesive.

Using part of the sealed braided sleeve 138 for the outer (mating) surface 136 of the sealing body 106 provides a surface that is smoother and more durable than would be provided by the silicone foam alone. This provides lower friction between the sealing body and the toroidal body 111, which makes it easier to adjust the axial position of the toroidal body, and enables the valve to be opened simply by releasing the pawl 110.

The part of the braided sleeve 138 extending distally from the sealing body 106 is called the sleeve extension 140. The sleeve extension passes through the bore of the toroidal body 111, and is attached to the valve body 100 by trapping it between the large luer hub 145 and the distal end 135 of the valve body. The large luer hub is preferably glued into the distal end of the valve body.

The braided sleeve 138 provides the sealing body 106 with tensile strength and locates the sealing body axially so that the sealing body can withstand the axial force applied to it by the toroidal body 111. The braided sleeve also provides a uniform radial compression to on the sealing body. The axial force exerted by the toroidal body 111 as it is advanced over the sealing body axially displaces the sealing body, and thus elongates the braided sleeve. The elongation of the braided sleeve provides a radial compression to the sealing body in addition to the radial compression provided by the juxtaposition of the mating surfaces 136 and 151 of the sealing body and the toroidal body, respectively.

The braided sleeve extension 140, being sealed with silicone sealant, provides a fluid-tight passage between the distal end 135 of the valve body and the distal end 126 of the sealing body.

FIG. 7 shows the surgical valve according to the invention in its open (non-sealing) position. The proximal end 141 of the toroidal body is slightly engaged with the distal end 126 of the sealing body; but the diameter of the outer surface 136 of the sealing body at distal end 126 is slightly reduced, so the toroidal body 111 does not deform the sealing body 106. Nor does the toroidal body 111 cause any elongation of the braided sleeve 138. Consequently, the axial passage 116 is not deformed, and no seal is formed with the catheter C in the axial passage.

Figure 8:
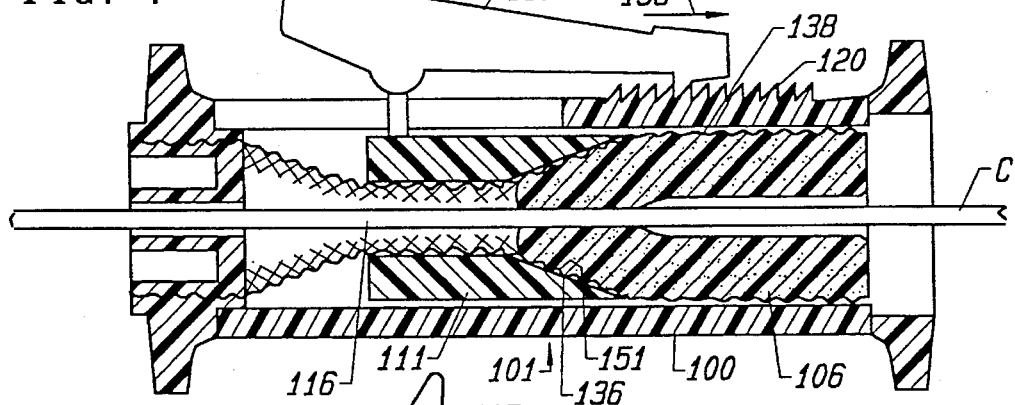
FIG. 8 is a longitudinal cross-sectional view of the first practical embodiment of an adjustable surgical valve according to the invention in its closed (sealing) position sealed around an instrument inserted into the axial passage of the valve.

FIG. 8 shows the surgical valve of FIG. 7 adjusted to form a minimum friction-no leakage seal with the catheter C. This adjustment can be carried out using only one hand. The valve body 100 is gripped in the fingers, and the pawl 110 is pulled by the thumb in the direction indicated by the arrow 156. The axial position of the pawl, and hence of the toroidal body 111, is adjusted to provide a seal that does not leak, yet imposes minimum friction on the catheter, and hence resistance to the movement of the catheter C. The low friction offered by the surgical valve according to the invention when adjusted in its minimum friction-no leakage positions provides maximum tactile feedback to the surgeon when inserting or adjusting an instrument, such as the catheter C, through the valve.

Moving the pawl 110 in the direction indicated by the arrow 156 moves the toroidal body 111 in the same direction and engages the inner surface 151 of the toroidal body with the outer surface 136 of the sealing body. The inner surface 151 deforms the outer surface 136 of the sealing body, moving it radially towards the axis. In addition, the axial movement of the toroidal body 111 moves the sealing body axially, which elongates the braided sleeve 138. The deformation of the outer surface 136 together with the elongation of the braided sleeve causes the wall of the axial passage 116 to move uniformly towards, and to seal with, the catheter C. The sealing body exerts an axial force on the toroidal body 111 in the direction opposite to that indicated by the arrow 156, but the toroidal body is prevented from moving by the pawl 111 engaged in the ratchet 120.

To release the valve completely, the valve body 100 is gripped in the fingers, and pressure is applied to the protrusion 125 with the thumb to release the pawl 110 from the ratchet 120. The axial force exerted by the sealing body 106 against the toroidal body 111 and the low friction between the braided sleeve 138 on the outer surface 136 of the sealing body and the inner surface 151 of the toroidal body makes the valve self-releasing. No axial pressure from the thumb is required to release the valve. To release the valve partially, the same procedure is used, except that the motion of the pawl is controlled, preferably by the thumb, and the pawl is re-engaged in the ratchet after the adjustment has been made.

Figure 9:
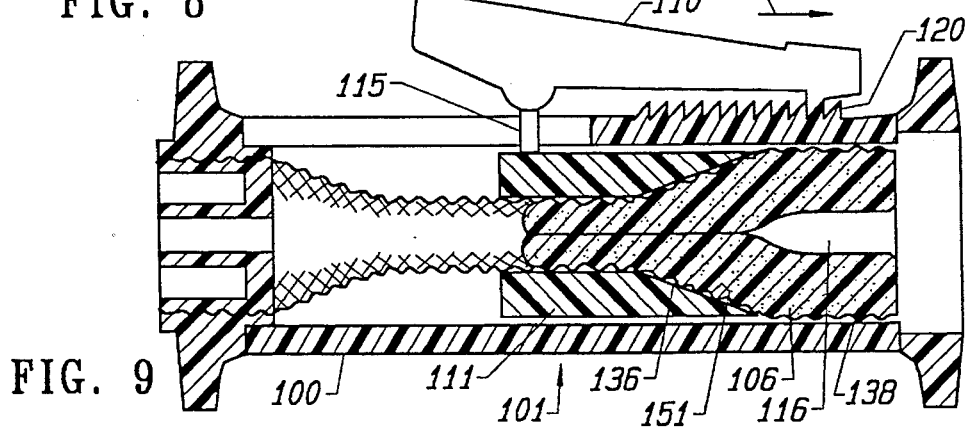
FIG. 9 is a longitudinal cross-sectional view of the first practical embodiment of an adjustable surgical valve according to the invention in its closed (sealing) position with the instrument removed.

FIG. 9 shows the surgical valve 101 according to the invention in its fully closed position, i.e., with no catheter inserted into the axial passage 116. The pawl 110, and hence the toroidal body 111, are moved further in the direction indicated by the arrow 156. This engages the inner surface 151 of the toroidal body still further with the outer surface 136 of the sealing body, and also increases the elongation of the braided sleeve 138. The increased radial deformation of the outer surface 136 of the sealing body further towards the axis and the increased elongation of the braided sleeve together cause the wall of the axial passage 116 to move radially towards the axis, to seal with itself. The material of the sealing body 106 is sufficiently compliant to allow the wall of the axial passage to seal with itself under moderate radial pressure. The pawl 110 and ratchet 120 hold the toroidal body 111 in its set axial position until the pawl is released.

The additional adjustment of the axial position of the toroidal body shown in FIG. 9 is only necessary when a large-diameter catheter is to be withdrawn from the surgical valve 101. In practice, when a large-diameter catheter is to be withdrawn from the valve, the valve is left set in the minimum friction-no leakage position shown in FIG. 8 until the catheter is almost completely withdrawn. The position of the pawl 110, and hence of the toroidal body 111, is then adjusted towards the position shown in FIG. 9. This increases friction, but still allows the catheter to be withdrawn. When the catheter disengages from the compressed part of the sealing body 106, the resilience of the sealing body 106 causes the part of the axial passage 116 under compression from the toroidal body 111 and the braided sleeve 138 to collapse radially towards the axis, and seal with itself. Depending on the diameter of the catheter C, the diameter of the sealing body 106, and the axial position of the toroidal body when the catheter is withdrawn, the pawl 110, and hence the toroidal body 111, may have to be moved further in the direction indicated by the arrow 156 to cut off residual leakage after the catheter has been withdrawn. With a smaller-diameter catheter, the valve adjusted to the minimum friction-no leakage position shown in FIG. 8 is self sealing, and no adjustment is necessary when the catheter is withdrawn.

Figure 10:
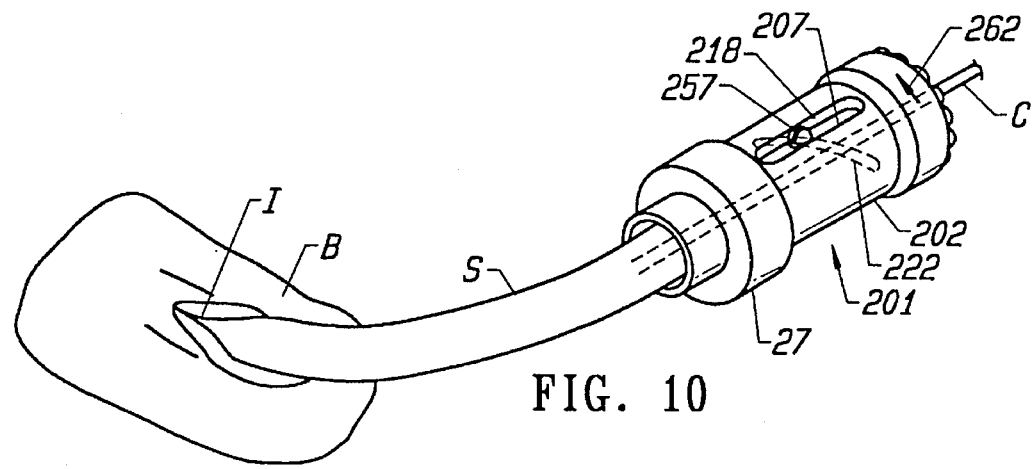
FIG. 10 is a perspective view of a second practical embodiment of an adjustable surgical valve according to the invention.
Figure 11:
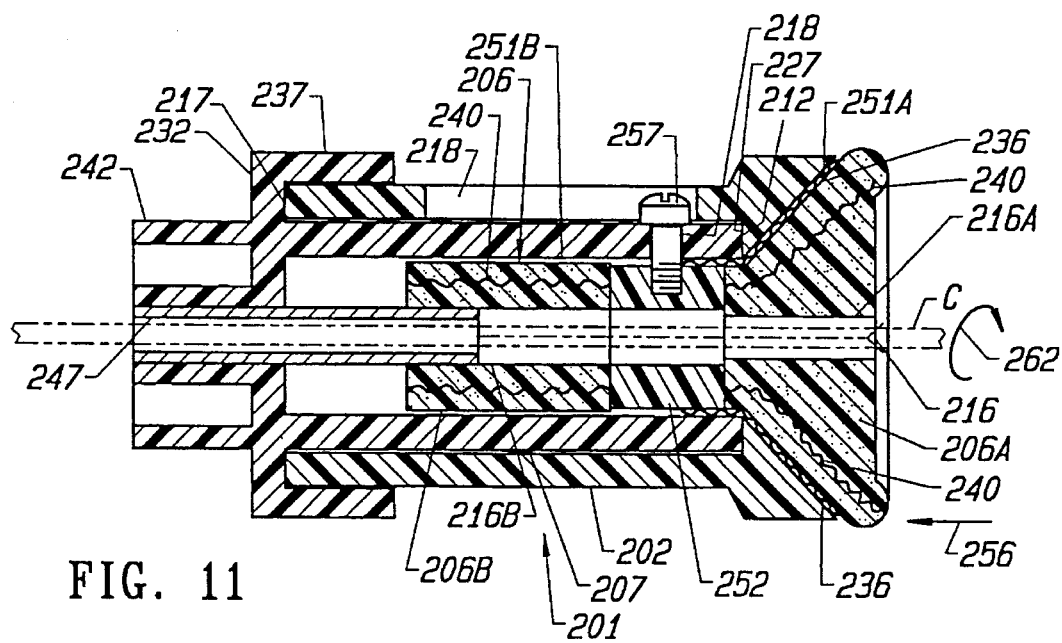
FIG. 11 is a longitudinal cross-sectional view of the second practical embodiment of an adjustable surgical valve according to the invention in its open (non-sealing) position.

FIGS. 10 and 11 show a perspective view and a longitudinal cross section, respectively, of a second practical embodiment of the surgical valve 201 according to the invention. In FIG. 10, the introducer sleeve S is sealed into the distal end of the surgical valve 201, and passes through an incision or puncture I in the body B. A catheter C passes through the valve 201 and the introducer sleeve S into the body B. The valve 201 has an outer valve body 202 and an inner valve body 207. The outer valve body 202 and the inner valve body 207 together form the toroidal body of the valve.

The outer valve body 202 is a hollow, substantially cylindrical polycarbonate plastic molding. The bore of the outer valve body 202 has a circular cross section, and is stepped towards the axis at its proximal end to form the shoulder 212, which provides a first thrust bearing for the inner valve body 207, as shown in FIG. 11. The distal end 217 of the outer valve body provides a second thrust bearing for the inner valve body 207. The bore of the outer valve body flares outwards proximally from the shoulder 212 to provide a first part of the inner surface 251A of the toroidal body of the valve. A longitudinal slot 218 is molded or cut in the outer valve body 202.

The inner valve body 207 is a hollow, substantially cylindrical polycarbonate plastic molding. The outer diameter of the inner valve body 207 is slightly smaller than the diameter of the bore of the outer valve body 202 so that the inner valve body can rotate freely within the outer valve body. The bore of the inner valve body provides a second part 251B of the inner surface of the toroidal body of the valve. A spiral slot 222, shown as a broken line in FIG. 10, is cut or molded in the wall of the inner valve body 207.

The proximal end 227 of the inner valve body mates with the shoulder 212 of the outer valve body to provide the first thrust bearing. The distal end of the inner valve body has a flange 232 that mates with the distal end 217 of the outer valve body to provide the second thrust bearing. Attached to the radially remote part of the flange 232 and coaxial with the inner valve body 207 is the twist ring 237. The twist ring 237 enables the inner valve body 207 to be gripped when the valve is adjusted.

A large luer hub 242 is attached to the distal end of the inner valve body 207, preferably by gluing with a suitable adhesive. Alternatively, and preferably, the large luer hub 242 can be an integral part of the inner valve body molding. The sealing tube 247 passes through the boss of the large luer hub coaxial to the inner valve body. The sealing tube is preferably an integral part of the inner valve body molding, but it can be a separate tube of metal, for example, stainless steel, or plastic.

In the second practical embodiment of the invention, the collar 252 longitudinally divides the sealing body 206 into a proximal part 206A and a distal part 206B, and divides the axial passage 216 into a proximal part 216A, which is in the proximal part 206A of the sealing body, and a distal part 216B. The proximal part 206A of the sealing body provides the main sealing action of the valve. The outer surface of the proximal part 206A of the sealing body provides the outer surface 236 of the sealing body. The distal part 206B of the sealing body 206B provides the required secondary seal between the static part of the valve, i.e., the sealing tube 247, and the moving part of the valve, i.e., the sealing body 206.

The diameter of the distal part 216B of the axial passage is slightly smaller than the outer diameter of the sealing tube 247, which allows the axial passage to form a fluid-tight seal with the sealing tube. The diameter of the proximal part 216A of the axial passage is about the same as the diameter of the bore of the sealing tube 247, and is thus smaller than the diameter of the distal part 216B of the axial passage.

In the plane perpendicular to the axis, the proximal part 206A of the sealing body has a circular cross section. Adjacent to the collar 252, the diameter of the proximal part 206A of the sealing body is slightly smaller than the diameter of the bore of the inner valve body 207. The diameter of the proximal part of the sealing body progressively increases in the direction proximal to the collar 252. The rate of increase of diameter is similar to the rate of increase of diameter of the inner surface 251A of the outer valve body 202.

In the plane perpendicular to the axis, the distal part 206B of the sealing body has a circular cross section with a substantially constant diameter. The outer diameter of the distal part of the sealing body is slightly smaller than the diameter of the bore of the inner valve body 207, so that the distal part of the sealing body can freely slide axially in the bore of the inner valve body.

The collar 252 is a plastic molding, preferably of polycarbonate. The outside diameter of the collar is slightly smaller than the diameter of the bore of the inner valve body 207, so that the collar can slide freely in the bore of the inner valve body. The bore of the collar is preferably larger than the outer diameter of the sealing tube 247. A radial hole is drilled and tapped in the side of the collar to receive the screw 257. The screw passes through the linear slot 218 in the outer valve body 202 and the spiral slot 222 in the inner valve body. A pin glued into the radial hole in the collar can be substituted for the screw. Twisting the outer valve body relative to the inner valve body in the direction shown by the arrow 262 (FIG. 10) moves the collar axially in the direction indicated by the arrow 256.

The sealing body 206 is formed by attaching a braided sleeve 240, which is preferably a substantially cylindrical piece of woven polyester material, to the bore of the collar 252, preferably by gluing with a cyanoacrylate adhesive. The collar and braided sleeve are then placed in a mold, and a suitable elastomeric foam is injected radially on both sides of the braided sleeve, and axially on both sides of the collar. Alternatively, the foam can be extruded around the braided sleeve and collar. The axial passage 216 is formed in the molding or extruding process. In the preferred embodiment, the sealing body is molded from Type 762 silicone foam manufactured by General Electric Co. Alternatively, the foam can be molded around the braided sleeve in a mold that provides a waisted area to receive the collar. The collar can then be attached to the exposed braided sleeve in the waisted area, preferably by gluing. The braided sleeve provides the elastomeric foam forming the sealing body with tensile strength, positively attaches the foam of the sealing body to the collar, and, when elongated, radially compresses the sealing body.

In this second embodiment, the braided sleeve 240 does not form the outer surface of the sealing body 206, as it does in the first embodiment. In the second embodiment, which lacks the pawl and ratchet arrangement of the first embodiment, some friction between the outer surface 236 of the sealing body and the inner surface 251A and 251B of the toroidal body is desirable to maintain the sealing body and the toroidal body in their desired relative axial positions. Because of this friction, the valve is not self-releasing: the outer valve body 202 must be twisted relative to the inner valve body 207 in the direction opposite to that indicated by the arrow 262 to release the valve. Alternatively, the friction between the outer surface of the sealing body and the inner surface of the toroidal body can be reduced, and the valve provided with a rotational pawl and ratchet or similar arrangement. Other mechanisms for changing the relative axial positions of the sealing body and the toroidal body can also be used in the second embodiment. For example, the linear pawl and ratchet arrangement of the first embodiment can be adapted for use in the second embodiment of the valve.

FIG. 11 shows the surgical valve according to the invention in its open (non-sealing) position. The inner surface 251A of the toroidal body lightly contacts the outer surface 236 of the sealing body such that the inner surface the toroidal body does not deform the outer surface of sealing body. Moreover, the inner surface of the toroidal body applies no axial stress to the sealing body, so there is no elongation of the braided sleeve 240. Thus, the axial passage 216A is not deformed.

Figure 12:
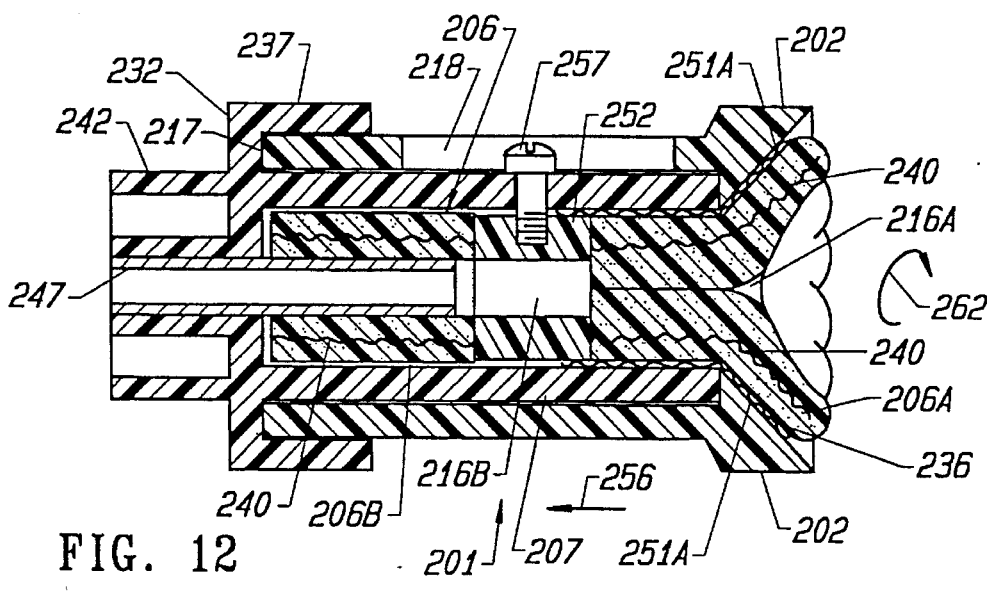
FIG. 12 is a longitudinal cross-sectional view of the second practical embodiment of an adjustable surgical valve according to the invention in its closed (sealing) position.

FIG. 12 shows the surgical valve of FIG. 11 adjusted to its fully sealing condition. The valve can be adjusted using only one hand. The gripping ring 237 is gripped by wrapping the middle finger around it and the proximal end of the outer valve body 202 is gripped between the thumb and forefinger. To seal the valve, the thumb and forefinger are moved relative to the middle finger to twist the outer valve body 202 in the direction indicated by the arrow 262. This causes the collar 252, and hence the sealing body 206, to move in the direction indicated by the arrow 256.

The collar 252 moving in the direction indicated by the arrow 256 draws the outer surface 236 of the sealing body into engagement with the inner surface 251A and 251B of the toroidal body. The rigid inner surface 251A and 251B of the toroidal body deforms the outer surface 236 of the sealing body moving it radially towards the axis. In addition, the toroidal body applies an axial stress to the sealing body, which elongates the braided sleeve 240. The deformation of the outer surface of the sealing body and the elongation of the braided sleeve together cause the wall of the axial passage 216A to move towards the axis, and, when the sealing body has been drawn far enough into the toroidal body, to seal with itself.

Drawing the sealing body further into the toroidal body increases the deformation of the outer surface of the sealing body and the elongation of the braided sleeve. This increases the length of the sealed part of the axial passage 216A and the inward radial pressure on the wall of the axial passage.

Like the first practical embodiment, the second practical embodiment of the surgical valve according to the invention can be adjusted to provide a "minimum friction-no leakage" seal around one or more catheters. Also, like the first practical embodiment, the second practical embodiment is self sealing from the minimum friction-no leakage position with a smaller-diameter catheter, and from a higher friction position with a larger-diameter catheter. The second practical embodiment of the valve can provide manual sealing of the valve, which the first practical embodiment cannot provide. When the second practical embodiment of the valve is in its open (non-sealing) position, the proximal end of the sealing body 206 projects proximally from the proximal end of the outer valve body 202, as shown in FIG. 11. The exposed part of the sealing body can therefore be gripped by an opposed thumb and finger, or by forceps, to provide manual sealing.

We claim:

1. A surgical valve comprising:

a sealing body having a smooth axial passage extending therethrough, the axial passage defining an axis, the sealing body having a position on the axis:

a toroidal body, axially aligned with the sealing body, and having a position on the axis, the sealing body and the toroidal body including mating surface means having a substantially circular cross section whereby changing the position of one of the sealing body and the toroidal body relative to the other creates a substantially uniform radial force to compress the axial passage of the sealing body; and a position changing means for selectively changing the axial position of one of the sealing body and the toroidal body relative to the other, wherein the position changing means moves the sealing body relative to the toroidal body.

2. A surgical valve comprising:

a sealing body having an axial passage extending therethrough, the axial passage defining an axis, the sealing body having a position on the axis;

a toroidal body, axially aligned with the sealing body, and having a position on the axis, the sealing body and the toroidal body having mating surface means whereby changing the position of one of the sealing body and the toroidal body relative to the other compresses the axial passage of the sealing body; and a position changing means for selectively changing the position of one of the sealing body and the toroidal body relative to the other;

wherein the mating surface means of the sealing body is of a cross section that increases along the axis from a minimum to a maximum; and wherein the mating surface means of the toroidal body is of a cross section that increases along the axis from a minimum to a maximum in the same direction as the direction in which the cross section of the mating surface means of the sealing body increases.

3. The surgical valve of claim 2, wherein:

the mating surface means of the sealing body is of a substantially circular cross section; and the mating surface means of the toroidal body is of a substantially circular cross section.

4. A surgical valve comprising:

a sealing body, the sealing body:
having an axial passage extending therethrough, the axial passage defining an axis, the sealing body having a position on the axis, and
including a braided sleeve coaxial with the axial passage, the braided sleeve extending from the sealing body to provide a remote part, the remote part having a position on the axis; and a position changing means for selectively changing the position of one of the sealing body and the remote part of the braided sleeve relative to the other to elongate the braided sleeve axially, thereby radially compressing the axial passage of the sealing body.

5. The surgical valve of claim 4, wherein the position changing means includes a toroidal body attached to the remote part of the braided sleeve.

6. The surgical valve of claim 5, wherein:

the sealing body has an outer surface;

the braided sleeve has an inner surface and an outer surface;

the toroidal body has an inner surface;

the sealing body is mounted within the braided sleeve with the outer surface of the sealing body attached to the inner surface of the braided sleeve; and the outer surface of the braided sleeve is attached to the inner surface of the toroidal body.

7. The surgical valve of claim 5, wherein:

the surgical valve additionally comprises a cylindrical valve body having a bore;

the sealing body is attached to the bore of the valve body; and the toroidal body is slidably mounted within the bore of the valve body.

8. The surgical valve of claim 4, wherein:

the surgical valve additionally comprises a cylindrical valve body having a bore;

the braided sleeve extends from the sealing body in a first direction to provide a first remote part;

the braided sleeve additionally extends from the sealing body in a second direction, opposite to the first direction, to provide a second remote part;

the sealing body and the braided sleeve are mounted within the bore of the valve body;

the position changing means is attached to the first remote part of the braided sleeve; and the second remote part of the braided sleeve is attached to the bore of the valve body.

9. A surgical valve comprising:

a substantially cylindrical valve body having a bore;

a sealing body slidably mounted coaxially in the bore of the valve body, and having an axial position therein, the sealing body having an axial passage extending therethrough, the axial passage defining an axis, the valve body and the sealing body having mating surface means whereby changing the axial position of the sealing body compresses the axial passage of the sealing body; and a means attached to the sealing body for selectively changing the axial position of the sealing body, at least in part by applying a tensile load on the sealing body.

10. The surgical valve of claim 9, further comprising a sealing tube in the bore of the valve body, the sealing tube being coaxial with the valve body, entering the axial passage of the sealing body, and forming a seal therewith.

11. The surgical valve of claim 9, wherein the valve body includes:

a substantially cylindrical outer valve body having a bore; and a substantially cylindrical inner valve body rotatably mounted in the bore of the outer valve body, and having a bore that provides the bore of the valve body.

12. The surgical valve of claim 11, wherein:

the inner valve body includes a spiral slot;

the outer valve body includes a longitudinal slot; and the means attached to the sealing body for selectively changing the axial position of the sealing body includes:

a collar attached to the sealing body, and a means, attached to the collar and engaging in the spiral slot and the longitudinal slot, for moving the sealing body axially when the outer valve body is rotated relative to the inner valve body.

13. The surgical valve of claim 9, wherein the sealing body comprises an encapsulated gel.

14. The surgical valve of claim 9, wherein the sealing body includes a braided sleeve which provides tensile strength.

15. A surgical valve comprising:

a substantially cylindrical valve body having a bore;

a sealing body slidably mounted coaxially in the bore of the valve body, and having an axial position therein, the sealing body having an axial passage extending therethrough, the axial passage defining an axis, the valve body and the sealing body having mating surface means whereby changing the axial position of the sealing body compresses the axial passage of the sealing body; and a means attached to the sealing body for selectively changing the axial position of the sealing body;

wherein the bore of the valve body provides the mating surface means of the valve body;

wherein the bore of the valve body is of a circular cross section that is substantially constant along the axis; and wherein the mating surface means of the sealing body is of a substantially circular cross section that increases along the axis in the direction away from the valve body.

16. A surgical valve comprising:

a substantially cylindrical valve body having a bore;

a sealing body slidably mounted coaxially in the bore of the valve body, and having an axial position therein, the sealing body having an axial passage extending therethrough, the axial passage defining an axis, the valve body and the sealing body having mating surface means whereby changing the axial position of the sealing body compresses the axial passage of the sealing body; and a means attached to the sealing body for selectively changing the axial position of the sealing body wherein the sealing body includes a braided sleeve attached to the means for selectively changing the axial position of the sealing body.

17. The surgical valve of claim 16, wherein the means for selectively changing the axial position of the sealing body is additionally for axially elongating the braided sleeve to contract the braided sleeve radially.

18. A surgical valve comprising:

a substantially cylindrical valve body having a bore;

a sealing body slidably mounted coaxially in the bore of the valve body, and having an axial position therein, the sealing body having an axial passage extending therethrough, the axial passage defining an axis, the valve body and the sealing body having mating surface means whereby changing the axial position of the sealing body compresses the axial passage of the sealing body; and a means attached to the sealing body for selectively changing the axial position of the sealing body;

wherein the sealing body comprises an encapsulated gel.

19. A surgical valve comprising:

a sealing body having a smooth axial passage extending therethrough, the axial passage defining an axis, the sealing body having a position on the axis, wherein the sealing body includes a braided sleeve which provides tensile strength;

a toroidal body, axially aligned with the sealing body, and having a position on the axis, the sealing body and the toroidal body including mating surface means having a substantially circular cross section whereby changing the position of one of the sealing body and the toroidal body relative to the other creates a substantially uniform radial force to compress the axial passage of the sealing body; and a position changing means for selectively changing the axial position of one of the sealing body and the toroidal body relative to the other.

* * * * *